:::
United States Patent [19]

Shiroshita et al.

[11] Patent Number: 5,118,815
[45] Date of Patent: Jun. 2, 1992

[54] METHOD FOR CRYSTALLIZATION OF AMINO ACIDS

[75] Inventors: Yoshinari Shiroshita; Ryuta Toyomasu; Masura Saeki, all of Saga, Japan

[73] Assignee: Ajinomoto Co., Inc., Tokyo, Japan

[21] Appl. No.: 582,846

[22] PCT Filed: Feb. 9, 1990

[86] PCT No.: PCT/JP90/00160
§ 371 Date: Oct. 15, 1990
§ 102(e) Date: Oct. 15, 1990

[87] PCT Pub. No.: WO90/09372
PCT Pub. Date: Aug. 23, 1990

[30] Foreign Application Priority Data
Feb. 13, 1989 [JP] Japan .................. 1-33369

[51] Int. Cl.$^5$ ................ C07D 209/20; C07C 229/42

[52] U.S. Cl. .................. 548/497; 562/433; 562/445; 562/554; 562/570

[58] Field of Search ........... 548/496, 497; 562/554, 562/445

[56] References Cited

U.S. PATENT DOCUMENTS 4,675,339  6/1987  Inoue et al. .................. 514/419

FOREIGN PATENT DOCUMENTS 46-19610   6/1971  Japan .
59-39857   3/1984  Japan .
60-237054 11/1985  Japan .

Primary Examiner—David B. Springer
Attorney, Agent, or Firm—Oblon, Spivak, McClelland, Maier & Neustadt

[57] ABSTRACT

A method for crystallization of an amino acid characterized by allowing a surfactant and/or an alcohol to exist upon crystallization.

3 Claims, No Drawings

METHOD FOR CRYSTALLIZATION OF AMINO ACIDS

FIELD OF THE ART

The present invention relates to a method for purification of amino acid, particularly to a method for crystallization of amino acid, more particularly to a method for improving crystal shape by crystallization operation of amino acid.

BACKGROUND ART

As conventional methods for crystallization of amino acid, there have been proposed a method for crystallization which comprises concentrating an aqueous solution of amino acid under reduced pressure, a method which comprises neutralization for crystallization, a method which comprises crystallization with a solvent while adding a lower alcohol or a ketone to the aqueous solution in large quantities, and so on (cf. Japanese Patent Application Laid-Open Nos. 59-39857, 59-45898, etc.).

Among these methods, in the method for crystallization which comprises concentration under reduced pressure, fine amino acid crystals precipitated tend to take bubbles in the crystals and cause bumping so that care must be required for the concentrating operation. Furthermore, according to the method which comprises neutralization for crystallization, crystals tend to float on the upper layer of the solution and the crystals do not grow as expected and in most cases, therefore, it might take time for solid-liquid separation. On the other hand, the method which comprises crystallization of amino acid by adding a lower alcohol or a ketone requires separate equipments for recovering the organic solvent, which not only leads to complicated process but is also economically disadvantageous, because it is impossible to completely recover the solvent.

Accordingly, it is significant in the art to provide a method for crystallization of amino acid having a high purity, in a simple manner using simple apparatuses.

DISCLOSURE OF THE INVENTION

The present invention relates to a method for crystallization of amino acid characterized by allowing a surfactant and/or an alcohol in an amino acid solution, upon crystallization of the amino acid.

MODE FOR PRACTICING THE INVENTION

The amino acid which is crystallized in the present invention is not particularly limited but preferred examples include phenylalanine, tryptophan, serine, isoleucine, valine, threonine and leucine. It is not particularly limited as how to prepare these amino acids but the amino acids may be any one prepared by fermentation, chemical synthesis, enzymatic method and other processes. In general, the present invention is applied to crystallization of L-amino acid but may also be applicable to D- or DL-amino acid and to amino acid derivatives.

The surfactant and alcohol which can be used in the present invention are as follows.

As anionic surfactants, there are effectively used fatty acid salt type, sulfate salt type, alkylallylsulfonate type and phosphate salt type. Specific examples include sodium oleate, sodium lauryl sulfate, sodium dodecylbenzenesulfonate, lecithin, etc.

As cationic surfactants, there are effectively used quaternary ammonium salt type, aliphatic amine type and pyridinium type. Specific examples include SANISOL (manufactured by Kao Atlas Co., Ltd.), laurylamine, lauryl hydrogensulfate pyridinium, etc.

As nonionic surfactants, there are effectively used polyoxyethylene ether type, sorbitan alkyl ester type, esters of polyvalent alcohols and fatty acids and fatty acid ethanolamide type. Specific examples include Brij (manufactured by Atlas Co., Ltd.), Tween (manufactured by Atlas Co., Ltd.), glycerol monostearate, etc.

As alcohols, polyvalent alcohols are effective. Specific examples include ethylene glycol, propylene glycol, etc.

Upon practice of the present invention, the additive described above is dissolved in an acid or alkali solution of amino acid and then adding an alkali or acid to the solution to effect crystallization by neutralization. Alternatively, after the additive described above is dissolved in an amino acid aqueous solution, the aqueous solution is concentrated to crystalize amino acid. In this case, however, since some of the additive is foaming, it is recommended to use such an additive that hardly foams, for example, glycerol monostearate, propylene glycol, etc. Alternatively, the amino acid aqueous solution in which the above additive is dissolved may be cooled as it is to cause crystallization. As stated above, the present invention is applicable, irrespective of crystallization of amino acid. In this case, a concentration of amino acid may be any concentration so long as crystals are precipitated. Furthermore, an amino acid composition is not particularly limited. It may also be of the system containing other impurities.

A concentration of the additive in the present invention greatly affect crystal mode and in some occasion, it is considered that crystal growth might be inhibited. Therefore, the optimum concentration has been previously determined by experiment. The concentration is generally 10 to 50000 ppm, preferably 500 to 5000 ppm, based on the weight of amino acid in the solution.

When the present invention is applied as described above, hydrophobic property of amino acid on the crystal surface is improved, its crystals form a stable suspension state without being isolated from the aqueous solution and, the substrate in the solution is continuously supplied to the crystal surface so that crystals grow to a large size without causing superfluous fine crystals. Accordingly, the crystals float on the surface of the aqueous solution only with difficulty and hence, the crystals can be readily concentrated, without taking foam therein and generating foam. The crystals further grow to a larger size and thus, operation for solid-solution separation also becomes easy and a volume of the mother liquor adhered can be reduced. In this case, the crystal mode varies in various fashions depending upon kind or concentration of the additive and method for crystallization. In general, however, the crystals tend to be aggregated by crystallization through concentration and in the case of crystallization by neutralization or cooling, tend to grow in a single crystal. As stated above, the present invention has established a technology for crystallization of amino acid in a high purity, by the addition of the surfactant.

Hereafter the present invention is explained in more detail, by referring to the examples.

EXAMPLE 1

To 1 liter of crude solution of pH 1.5 containing L-phenylalanine (L-Phe) in a concentration of 150 g/liter was added 1000 ppm each (based on the weight of L-Phe) of the additive shown in Table 1. After crystals were precipitated by neutralizing at 60° C. to pH of 6.0, the system was cooled to 40° C. to grow the crystals. The obtained crystals were isolated for evaluation under definite conditions using a desk centrifuging machine. For purpose of comparison, the same operation was performed in the case where no additive was added. The results are shown in Table 1.

TABLE 1

| Additive | Purity of Crystal | Water Adhered | Shape of Crystal (size) |
| --- | --- | --- | --- |
| Sodium laurylsulfate | 97.2% | 1.9% | Aggregate of several single crystals (40–80 μm) |
| Span 20 (manufactured by Atlas) | 94.4% | 3.9% | Aggregate of large, thick crystals (100–200 μm) |
| TL-10 (manufactured by Japan Chemicals) | 88.3% | 7.6% | Aggregate of fine crystals (containing in part fine crystals) (20–40 μm) |
| Glycerol monolaurate | 87.8% | 8.9% | Aggregate of fine crystals (containing in part fine crystals) (10–40 μm) |
| Fatty acid sucrose ester | 82.6% | 10.8% | Aggregate of fine crystals (containing in part fine crystals) (20–50 μm) |
| Propylene glycol | 80.8% | 14.8% | Aggregate of rhombic crystals (70–140 μm) |
| None | 70.9% | 21.2% | Aggregate of fine crystals (10–20 μm) |

EXAMPLE 2

To 5 liters of an aqueous solution containing L-tryptophan (L-Trp) in a concentration of 6 g/liter, which had been obtained by fermentation, was added 2000 ppm each (based on the weight of L-Trp) of the additive shown in Table 2. After the aqueous solution was concentrated under reduced pressure at 60° C., it was cooled to 40° C. to precipitate the crystals of L-Trp. The obtained crystals were isolated for evaluation under definite conditions using a desk centrifuging machine. For purpose of comparison, the same operation was performed in the case where no additive was added. The shape of crystals and suspension state in this case are shown in Table 2.

TABLE 2

| Additive | Water Adhered | Shape of Crystal and Suspension State |
| --- | --- | --- |
| Glycerol monostearate | 38.1% | Somewhat large size, good deposition, no foaming |
| Softazolin (manufactured by Kawaken Fine Chemicals) | 45.2% | Aggregate of spherical crystals, foaming only with difficulty |
| TL-10 (manufactured by Japan Chemicals) | 48.4% | Scaly crystals, foaming only with difficulty |
| Propylene glycol | 51.8% | Scaly crystals, foaming only with difficulty |
| None | 57.3% | Fine scaly crystals easy to float, foaming |

EXAMPLE 3

To 2 liters of an acidic solution obtained by dissolving crude L-isoleucine (L-Ile) crystals in a concentration of 250 g/liter at 50° C., was added 500 ppm each (based on the weight of L-Ile) of the additive shown in Table 3. After crystals were fully dissolved, 6N-NaOH aqueous solution was dropwise added to the solution for neutralizing to recrystallize. The crystals were isolated by filtration for evaluation under definite conditions. For purpose of comparison, the same operation was performed in the case where no additive was added. The shade of crystals and suspension state in this case are shown in Table 3.

TABLE 3

| Additive | Water Adhered | Shape of Crystal and Suspension State |
| --- | --- | --- |
| Lauryl hydrogen-sulfate pyridinium | 15.8% | Scaly, hard to float. Good suspension state is obtained. |
| Laurylamine | 17.5% | Scaly |
| Ethylene glycol | 20.1% | Scaly, hard to float. Good suspension state is obtained. |
| Span 20 (manufactured by Atlas) | 20.3% | Scaly, foaming only with difficulty |
| Brij 35 (manufactured by Atlas) | 22.3% | Aggregate of fine crystals, somewhat foaming |
| Lecithin | 22.9% | Aggregate of fine crystals |
| None | 26.7% | Fine scaly crystals, easy to float |

Industrial Applicability

According to the present invention, operability for isolating amino acid crystals can be improved and at the same time, crystals having a higher purity can be prepared at low costs. Therefore, it is expected to practice the present invention on an industrial level.

We claim:

1. A method for crystallization of an amino acid selected from the group consisting of phenylalanine, tryptophane, serine, isoleucine, valine, threonine and leucine comprising (1) dissolving a surfactant, a polyvalent alcohol or a mixture thereof in an acid or alkali solution of said amino acid and then adding an alkali or acid to the solution to effect crystallization by neutralization, or (2) dissolving a surfactant, a polyvalent alcohol or a mixture thereof in an aqueous solution of said amino acid and then concentrating the aqueous solution to effect crystallization, or (3) dissolving a surfactant, a polyvalent alcohol or a mixture thereof in an aqueous solution of said amino acid and then cooling the aqueous solution to effect crystallization.

2. A method for crystallization of said amino acid according to claim 1, wherein said surfactant is at least one of an anionic surfactant of fatty acid salt type, sulfate salt type, alkylallylsulfonate type and phosphate salt type; a cationic surfactant of quaternary ammonium salt type, aliphatic amine type and pyridinium type; and a nonionic surfactant of polyoxyethylene ether type, sorbitan alkyl ester type, ester of polyvalent alcohols and fatty acid and fatty acid ethanolamide type.

3. A method for crystallization of said amino acid according to claim 1, wherein said polyvalent alcohol is selected from the group consisting of ethylene glycol and propylene glycol.

* * * * *